United States Patent [19]

Semerdjian

[11] Patent Number: 5,653,777
[45] Date of Patent: Aug. 5, 1997

[54] BONDING PROCEDURE FOR SILICA ASSEMBLIES

[75] Inventor: Roy Vahan Semerdjian, Fair Oaks, Calif.

[73] Assignee: UOP, Des Plaines, Ill.

[21] Appl. No.: 545,492

[22] Filed: Oct. 19, 1995

[51] Int. Cl.⁶ ........................................ C03B 8/00
[52] U.S. Cl. ........................ 65/17.2; 427/376.2; 156/89
[58] Field of Search .................... 65/17.2; 427/376.2, 427/601; 156/89

[56] References Cited

U.S. PATENT DOCUMENTS 4,293,325  10/1981  Chirino et al. .................. 65/43
4,476,156  10/1984  Brinker et al. ................. 427/82
4,888,036  12/1989  Clasen ........................... 65/18.1

Primary Examiner—Donald E. Czaja
Assistant Examiner—Jacqueline A. Ruller
Attorney, Agent, or Firm—Thomas K. McBride; John G. Tolomei

[57] ABSTRACT

A method for bonding silica containing materials uses a mixture of ultrasonically treated silica powder and a suspension liquid to provide a bonding material. Once applied to the bonding surfaces of silica containing components the mixture is dried and then heated. Upon cooling the mixture provides a solid bonding between the components. The bonding procedure minimizes the mount of localized heating required to bond the material and thereby prevents distortion of silica components as they are bonded.

13 Claims, 2 Drawing Sheets

BONDING PROCEDURE FOR SILICA ASSEMBLIES

FIELD OF THE INVENTION

This invention relates generally to assemblies made of fused silica components and the bonding of fused silica components to substituently similar components.

BACKGROUND OF THE INVENTION

Fused silica has found wide spread use as a capillary tubing material for gas chromatography applications and in glass on glass optical waveguide fibers. Practical arrangements for fixing fused silica capillaries and fibers to other silica containing components in equipment has presented a number of challenges. For example direct melt bonding of fine fused silica components to relatively larger silica supporting structures has caused unacceptable deformation or not provided adequate structural strength.

The construction of spiral-wound capillary assemblies for gas chromatography exemplifies the problems associated with joining fused silica capillary tubing to a support structure. The arrangement is fully described in copending application U.S. Ser. No. 08/394,127, filed on Feb. 24, 1995, the contents of which are hereby incorporated by reference, and uses a fused quartz mandrel to support multiple windings of fused silica capillary tubes about the mandrel. A connection communicates an end of the capillary tube with metallic tubing via a fused silica body joined to the mandrel. Contact of the capillary tube with the mandrel and simultaneous or subsequent heating did not provide enough bonding to prevent ready peeling of the capillary windings from the mandrel.

The attachment of connections to thin capillary tubing has also proven difficult. U.S. Ser. No. 08/545,080 filed on Oct. 19, 1995, the contents of which are hereby incorporated by reference, discloses a connector arrangement for withdrawing gases from the previously described arrangement of capillary tubing attached to the mandrel. The high heat capacity of the mandrel relative to the small capillary tubing causes ordinary melt bonding to again result in excessive deformation of the capillary and the fused silica body of the connection or the mandrel.

Therefore improved methods are sought for bonding the silica containing materials of the mandrel, capillary and connector body.

SUMMARY OF THE INVENTION

A bonding procedure has now been discovered that will bond fused silica components to other silica containing materials at temperatures as low as 1500° C. to provide structures of improved strength, durability and dimensional consistency. Thus, this invention is a bonding procedure that uses a specially prepared sol gel to provide a bonding solution which after application to a bonding surface of silica containing material and subsequent heating and cooling which will result in a high strength bond. The bonding procedure produces strong bonds between silica containing components without excessive heat. The sol gel reduces the total energy needed to fuse the fused silica components together. Filling the gap between the two components with the silica sol gel prior to fusing improves thermal conduction and reduces the heat required for bonding. In turn, reduced heat means reduced distortion of external surfaces. Therefore, the bonding method of this invention allows the fusion of silica components at lower bonding temperatures to minimize or eliminate the distortion of the resulting bonded structures.

Accordingly, in one embodiment the invention is a method for surface bonding of fused silica materials. The method ultrasonically treats a mixture of a silica powder and a suspension liquid. The silica powder has a maximum particle size of 0.5 µm. The ultrasonically treated sol gel mixture is applied to a bonding surface comprising a fused silica material in a relatively uniform coating. After application to the bonding surfaces, the mixture is dried by evaporating the solvent from the bonding surface. After drying the bonding surface is heated to a temperature of least 1500° C. Once cooled, the solidified deposit from the mixture is integrated into the surface to which it was applied and together with the components to which it was applied forms a unitary body.

In a more specific embodiment the method of this invention bonds fused silica materials by first forming a mixture of silica powder and an alcohol. The mixture contains at least 20% by weight of an alcohol. The silica powder has a 0.5 µm maximum particle size and also contains a germanium and phosphorous oxides. The mixture is first blended for at least 5 minutes and then ultrasonically treated for at least 30 minutes. After blending, the treated mixture is again applied in a relatively uniform coating to the surfaces of components comprising fused silica while the surfaces of the components are held in contact. The mixture is dried to evaporate the alcohol and then the bonding surfaces are heated to a temperature of at least 1500° C. Subsequent cooling yields a solid bond between the components that integrates the bonding mixture.

DETAILED DISCLOSURE OF THE INVENTION

Figure 1:
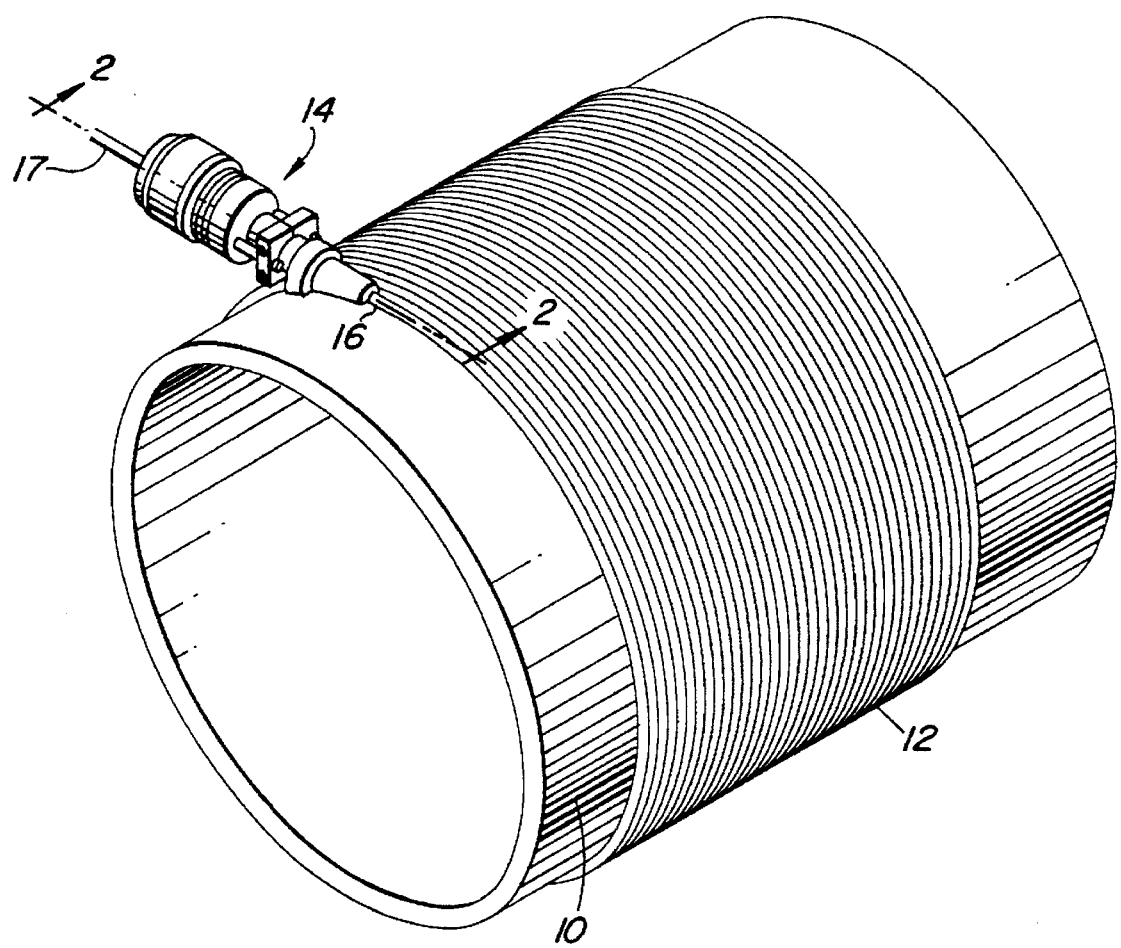
FIG. 1 is a three dimensional view showing a mandrel, spiral wound capillary tubing, and a connector.

The bonding procedure of this invention is a highly useful procedure for bonding fused silica components. The bonding method of this invention is generally applicable to the bonding of amorphous silica containing components and especially useful for the bonding of precision components formed from amorphous fused silica.

An essential element of this invention is the use of a sol gel to provide a source of silica that provides an integral silica bonding material in the joining of the silica-containing components. The suitable silica sol gel mixture will facilitate the deposition of a uniform coating of the component parts with the mixture to provide the integral silica bonding material. The sol gel mixture will comprise a silica powder consisting of small particles with a maximum particle diameter of 0.5 µm. The silica sol gel may include particles having smaller diameters than 0.5 microns. The silica powder that forms the base material for the sol gel may also include germanium oxide and phosphorus oxide components within the silica powder. The melting point modifications provided by such components has been found to enhance the depositing and the bonding strength of the silica bonding material once formed. The silica powders may contain 1–10 wt % of germanium and/or phosphorous oxide components. The powders will typically contain a combination of germanium oxide and phosphorus oxide components, preferably in a combined amount of from 1–10 wt %. A suitable source of sol gel materials is from the Gel Tech Company located in Alachua, Fla.

The bonding material is first formed by combining the silica powder with a liquid that will keep the powder in suspension and provide the necessary bonding properties. Suitable liquid vehicles of suspension liquids for forming the sol gel material will be relatively inert to the silica powder but will provide sufficient viscosity to the mixture to keep the sol gel material in suspension during application of the sol gel to the bonding surfaces. The suspension should also have a high volatility to promote rapid drying of the bonding material after its application to a surface. Suitable solvents include alcohols, ketones, and aldehydes—with the alcohols being preferred. A particularly preferred solvent is ethyl alcohol. Water is also a possible solvent; however, its use is not preferred due to the extended drying time required after an application of the sol gel mixture.

Liquid is added to the mixture in an amount to provide a suitable vehicle for distributing the solids evenly over the surface or between the components receiving the coating of bonding material while yet providing sufficient viscosity to prevent excessive run off of the solution before it drys. The mixture of silica powder and the suspension liquid will contain at least 20% by weight solids and may contain up to 70 wt % solids. Preferably the mixture will be a 50/50 mixture of alcohol and Gel Tech silica powder.

Treating of the sol gel mixture by ultrasonic treatment has also been found to influence the performance of the bonding material in subsequent steps. Ultrasonic treatment of the sol gel material improves its bonding characteristics and its formation of an integral bond material with the silica components. While not wishing to be bound to any particular theory the ultrasonic treatment of the sol gel is believed to enhance the performance of the bonding material by providing a more uniform coating of the material. Ultrasonic treatment should last for a period of at least 10 minutes and, more preferably, for at least 30 minutes. In the preferred treating procedure for the sol gel mixture, it is first shaken for a period of at least 5 minutes and then ultrasonically treated for at least 30 minutes.

Coating of component parts with the sol gel mixture, continues the bonding procedure. It is an important aspect of this invention that the sol gel be applied as a nearly uniform layer. Achieving high strength bonds by the method of this invention requires a relatively uniform coating. Application of the bonding material in a uniform layer prevents the formation of voids and gaps that can lead to further failure of the bonded components. Again, ultrasonic treatment of the sol gel is believed to provide complete dispersion of the sol gel to achieve good flow and a uniform coating of the sol gel. Suitable application techniques should provide a coating having a thickness of from 50 microns to 200 microns or more. Suitable application methods will produce a relatively uniform coating. By relatively uniform, it is meant that variations of the coating thickness will generally vary by less than 50% of its average depth.

The sol gel mixture may be applied between surfaces of components that are directly in contact for fusing. It has also been found that the sol gel material will wick into gaps and grooves to fill in void spaces and provide a continuous deposit of bonding material. The sol gel material should be applied before the surfaces to be bonded are brought into contact or may be allowed to wick into preset grooves or spaces bordered by the surfaces to be bonded. Any method can be used to hold silica components in place after the sol gel material has been applied or while it is being applied. An oxy-hydrogen torch is a convenient method of tacking silica components into place. In a preferred method the components are held in place by forming small ligaments of melted material, the sol gel material is then put in place by a method appropriate for the size of the components.

The sol gel material should be applied to a surface at ambient temperature. The alcohol content of the sol gel material may be adjusted to provide sufficient viscosity to retain a relatively uniform coating of the sol gel in place while it dries. Any method can be used to provide a relatively uniform coating of the sol gel mixture. A dipping procedure may provide a satisfactorily uniform coating over large bonding surfaces. For contact surfaces or the wicking of the mixture into grooves, free wire or filaments may provide a suitable applicator for dipping into the sol gel material and dropping droplets of the sol gel around the edges of fused silica materials.

Once placed on the bonding surfaces, the sol gel material is allowed to dry completely. The drying time should be sufficient to evaporate the suspending liquid in the sol gel and leave a relatively dry deposit from the treated silica mixture. Drying of the preferred ethyl alcohol suspension liquid from the sol gel mixture at ordinary conditions will usually take about five minutes. After drying, the sol gel material will typically appear as a totally opaque coating on the bonding surfaces.

Heating of the dried sol gel material transforms it into an integral bonding material. The specific heating temperatures required for transformation of the deposited silica material and integral bonding with the components will vary depending on the melt point of the fused silica components. Typically, the suitable temperatures will be in a range of from 1500° C. to 1650° C. for most fused silica compositions with temperatures of less than 1600° C. being preferred. Heating may be accomplished by any procedure which will fuse the dried sol gel material into an integral glass deposit formed about the joint components. For small components, localized heating with an oxy-hydrogen micro torch can raise the temperature of the components sufficiently to fuse the dried sol gel deposit and the components. Preferably, the heating technique will raise the temperature of the components and sol gel deposit to about the minimum required to fuse the bonding material and components. The minimum temperature is typically about 1500° C. A gradual heating technique is preferred to avoid overheating of the surfaces. For larger components, heating with a flame or oven treatment may be necessary to evenly distribute heat across a sufficient area of the joint components to provide an effective bonding technique.

After heating has integrally fused the sol gel material to the silica components, the components are cooled. Cooling yields an integral one piece structure consisting of the joined components and the fused silica material which now appears completely clear.

If localized heating has been used to fuse the sol gel material to the components, any remaining opaque deposits of sol gel material which did not receive adequate heating may undergo further heat treatment to clarify the structure. Annealing of the final structures to temperatures of from 1200° to 1400° C. will usually turn any remaining silica deposits to completely clear.

The particular application of this invention to the bonding of fused silica capillary tubing to connectors and a supporting mandrel for gas chromatography is described in conjunction with the drawings. Those skilled in the art will readily recognize other arrangements of fused silica components that can utilize this invention with other configurations of fused silica components and the description of this invention in the context of fused silica tubing arrangements is not meant to limit the scope of this invention thereto.

This bonding arrangement is specifically suited for this particularly advantageous chromatography arrangement that wraps multiple windings of the fused silica capillary tubing around a mandrel. Typical capillary tubing used with this invention will have outer diameters of less ranging from 250 to 650 μm with capillary bores sizes of from 75 to 530 μm. FIG. 1 shows a typical arrangement of this type having a mandrel 10 with multiple windings of capillary tubing 12. The bonding procedure of this invention is used to provide additional surface area to more firmly secure the capillary tubing to the surface of mandrel 10. The bonding procedure begins with the preparation of a sol gel solution consisting of a 50/50 mixture by weight of ethyl alcohol and a silica powder containing 0.5 micrometer silica particles. The sol gel mixture undergoes shaking for 5 minutes and ultrasonic treatment for at least 30 minutes before application to the tube surfaces. After ultrasonic treatment of the sol gel material, it is applied to the mandrel by dipping the bottom surface of the mandrel into a bath of the sol gel mixture and rotating the mandrel until a complete coating of the sol gel mixture has been applied to its outer surface. Dipping and rotation of the mandrel produces a coating of bonding material having a depth of about 50 microns on the surface of the mandrel. The sol gel mixture is then allowed to dry in the manner previously described. After the deposited sol gel material has dried, an oxy-hydrogen torch heats about a half inch section of the mandrel as the mandrel is rotated. The heating and rotation provides a uniform hot band around the mandrel having a temperature of about 1600° C. Winding of the capillary tubing about the mandrel as it rotates with a crossfeed mechanism provides a uniform winding of the capillary tube as the heat source moves the hot band axially over the entire length of the mandrel. Following completion of the windings, the cooling of the mandrel yields a composite structure having capillary tubes integrally bonded to the mandrel by the fused bonding material of the sol gel. Annealing of the capillary and mandrel composite structure of temperatures of 1200° to 1400° C. removes any opacity associated with insufficiently heated sol gel materials.

FIG. 1 also shows a connector arrangement 14 that communicates an end 16 of capillary tubing 12 with metallic tubing 17. Previously referenced U.S. Ser. No. 08/545,080 contains a full description of the connector arrangement. Looking at FIG. 2 the connector arrangement requires the attachment of a tube in the form of a fused silica connector body 18 that forms an interface between the capillary tube 16 and the metallic tubing 17. The fused silica body will typically have a diameter of from 3 mm to 8 mm. Metallic tubing 17 conducts liquids or gases from the interior of the capillary tubing through connector body 18 to suitable equipment for the collection and analysis of the material recovered from the capillary tubes.

Figure 2:
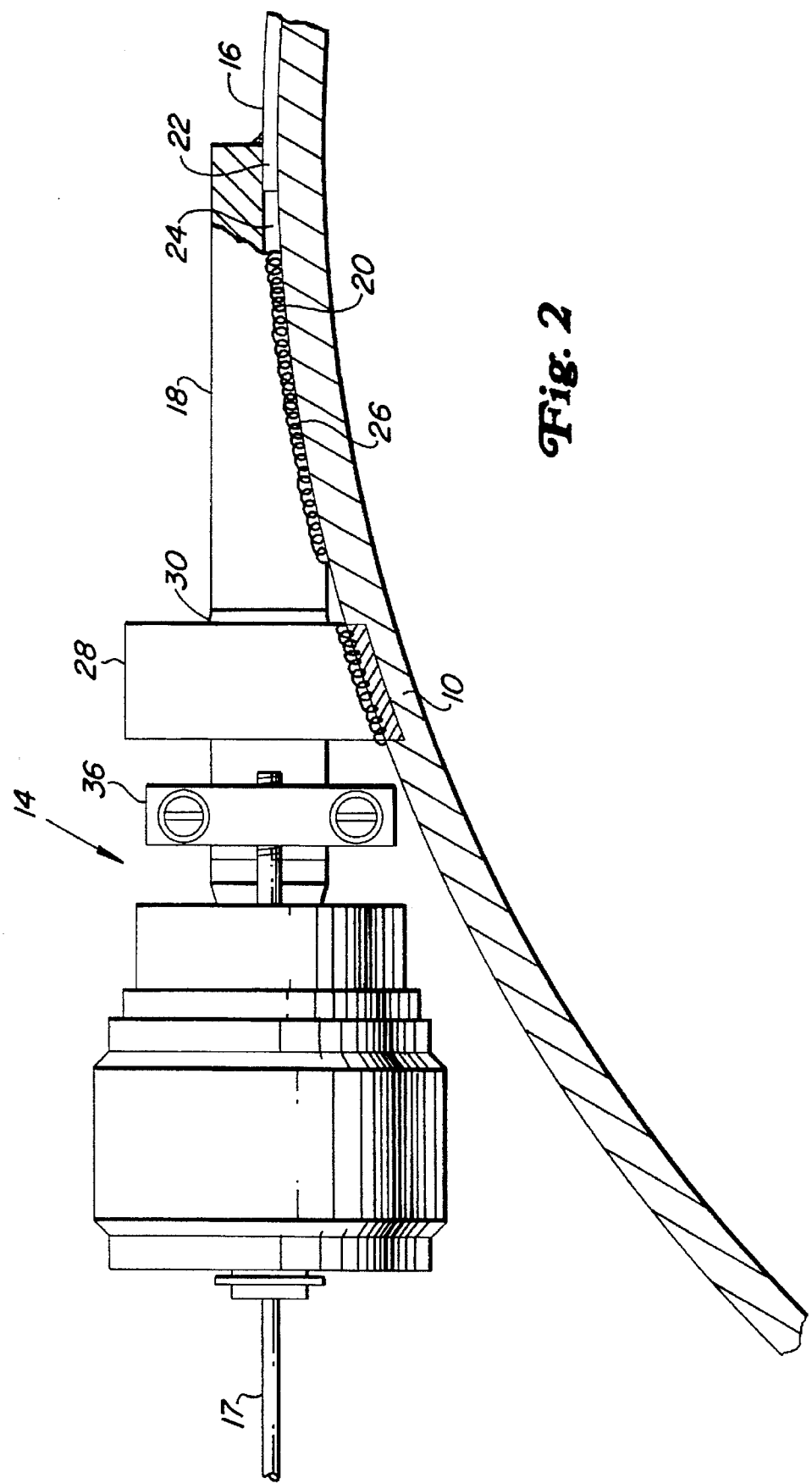
FIG. 2 is a enlarged view of bonding areas between the connector, mandrel, and capillary tubing.

The mandrel 10 typically consists of a silica material similar to the silica body. Lapping the end of the connector body that contacts the mandrel produces a sloped contact surface 20 that conforms to the radius of the mandrel 10. The lapping procedure also removes sufficient material from the connector body to create a longitudinal slot from the central bore of the connector body for receiving the end 16 of capillary tube 12. A cut away view in FIG. 2 depicts the end of connector body 18 showing the longitudinal slot 24 formed by the end of connector body 18 that overlaps end 22 of the capillary tube.

Once the connector body is in place over the mandrel, an oxygen/hydrogen micro torch is used to tack the connector body 18 over the capillary end and onto the mandrel. Permanent fusing of connector body 18 to mandrel 10 begins with the preparation of a sol gel solution consisting of a 50/50 mixture by weight of ethyl alcohol and a silica powder containing 0.5 micrometer silica particles. The sol gel mixture undergoes shaking for 5 minutes and ultrasonic treatment for at least 30 minutes before application to the tube surfaces.

The sol gel mixture is then applied to the mandrel, connector body and capillary tube at ambient temperatures using a thin gauge applicator such as a wire to put droplets of the sol gel mixture over the components at the edges of the components. The droplets of the sol gel mixture are wicked into the spaces between the body 18 and the mandrel to form a uniform coating of the sol gel having a thickness of about 100 μm. The sol gel also wicks into small spaces between the outside of the capillary and silica body. After the applied sol gel mixture has dried thoroughly, slow heating with a micro torch is carried out up to a temperature of about 1600° C. During heating the sol gel clarifies and the bond is completed. Bonding material 26 made of a sol gel material seals the end of the connector body in place over the mandrel and capillary end to form a unitary structure. The connector will also typically employ a clamp 28 which may be attached to the mandrel in the same manner as body 18.

What is claimed is:

1. A method for bonding materials comprising fused silica containing components, said method comprising:

shaking a mixture of a silica powder having a 0.5 μm maximum particle size and a suspending liquid to produce a shaken mixture;

ultrasonically treating the shaken mixture to produce a treated sol gel mixture;

applying a coating of said treated sol gel mixture to a bonding surface comprising a fused silica material;

evaporating said suspending liquid from said bonding surfaces;

heating said bonding surface to a temperature of at least 1500° C., and cooling said bonding surface to produce an integral deposit of silica bonding material on said bonding surface.

2. The method of claim 1 wherein said suspending liquid comprises an alcohol.

3. The method of claim 2 wherein said alcohol comprises ethyl alcohol.

4. The method of claim 2 wherein said mixture comprises 50% percent alcohol and 50% silica powder by weight.

5. The method of claim 1 wherein said ultrasonic treatment has a duration of at least 30 minutes.

6. The method of claim 1 wherein said suspension liquid is evaporated at ambient temperature.

7. The method of claim 1 wherein said coating has a thickness of from 50 to 200 μm.

8. The method of claim 1 wherein said coating is applied to produce a relatively uniform thickness.

9. The method of claim 1 wherein said bonding surface is heated to a temperature that does not exceed 1600° C.

10. The method of claim 1 wherein said silica powder contains up to 10 wt % of germanium and/or phosphorous oxide components.

11. A method for bonding the surfaces of materials comprising fused silica, said method comprising:

forming a mixture by mixing a silica powder having a 0.5 µm maximum particle size and a germanium oxide and a phosphorous oxide component with an alcohol to form a mixture comprising at least 20 wt % solids;

blending said mixture for at least 5 minutes;

ultrasonically treating the blended mixture for at least 30 minutes;

applying a uniform coating of said treated mixture to the bonding surfaces to form coated surface of components comprising fused silica and evaporating said alcohol from said coated surfaces;

maintaining said coated surfaces in contact;

heating said coated surfaces to a temperature of at least 1500° C.; and, cooling said bonding surfaces to yield an integral deposit of silica bonding material between the coated surfaces of said components.

12. The method of claim 11 wherein said alcohol comprises ethyl alcohol.

13. The method of claim 11 wherein said alcohol and said powder are mixed in equal weight proportions.

\* \* \* \* \*

UNITED STATES PATENT AND TRADEMARK OFFICE
CERTIFICATE OF CORRECTION

PATENT NO: 5,653,777
DATED: 8/05/97
INVENTORS: ROY VAHAN SEMERDJIAN

It is certified that error appears in the above-identified patent and that said Letters Patent is hereby corrected as shown below:

In Claim 1, column 6, line 45, the word "surfaces" should be "surface".

Signed and Sealed this

Twenty-first Day of October 1997

Attest:

BRUCE LEHMAN

Attesting Officer

Commissioner of Patents and Trademarks